United States Patent [19]

Lo et al.

[11] Patent Number: 4,870,189

[45] Date of Patent: Sep. 26, 1989

[54] PROCESS FOR SYNTHESIS OF AZETIDINE AND NOVEL INTERMEDIATES THEREFOR

[75] Inventors: Young S. Lo; Dwight A. Shamblee; David H. Causey, all of Richmond; Richard P. Mays, Ashland, all of Va.

[73] Assignee: A. H. Robins Company, Incorporated, Richmond, Va.

[21] Appl. No.: 7,596

[22] Filed: Jan. 28, 1987

[51] Int. Cl.$^4$ .................................... C07D 205/04
[52] U.S. Cl. .................................... 548/954; 548/950
[58] Field of Search .................. 548/950, 954

[56] References Cited

U.S. PATENT DOCUMENTS 3,336,294  8/1967  Miller et al. .................. 548/954
4,529,544  7/1985  Renga .......................... 548/950
4,634,554  1/1987  Wood et al. ................... 548/950

OTHER PUBLICATIONS

Nitta and Kanamori, "Synthesis of Azetidine from 1-Substituted Azetidin-3-ols", Heterocycles, vol. 24, No. 9, 1986, pp. 2467-2470.

Szmuszkovicz et al., "New Synthesis of Azetidine", J. Org. Chem. 1981, 46, 3562-3564.

*Primary Examiner*—Mukund J. Shah
*Assistant Examiner*—C. L. Cseh

[57] ABSTRACT

A novel process is described for preparing azetidine and 2 or 3 methyl and ethyl azetidine free bases by reacting primary arylmethylamine having suitable bulk providing substituents attached to the methyl carbon and an appropriate propane derivative having leaving groups in the one and three position in hot organic solvent containing a non-nucleophilic base and an amount of water sufficient to promote azetidine ring formation to give N-protected-azetidines and deprotecting by hydrogenolysis under acidic conditions to give an acid salt of the azetidines and thereafter flashing off vaporized azetidine from a hot, agitated strong base solution or slurry and condensing to give the liquid azetidine free bases.

21 Claims, No Drawings

PROCESS FOR SYNTHESIS OF AZETIDINE AND NOVEL INTERMEDIATES THEREFOR

BACKGROUND OF THE INVENTION

1. Field of Invention

This invention relates to a novel process for the preparation of azetidine and 2 or 3-methyl and ethyl azetidine free bases starting with an α-substituted arylmethyl amines and an appropriate propane derivative having leaving groups in the 1 and 3 positions. The invention encompasses novel intermediates, use thereof, and methods of preparation and a novel method of obtaining the azetidines in free base form from their mineral acid salts.

2. Information Disclosure Statement

Azetidine is available commercially only in small quantities. Szmuszkovicz, J., et al. in J. ORG. CHEM. (1981) 46, 3562-3564 prepared azetidine by heating tri-n-butylphosphoranilidine-1-propanol. They also discussed the work of others wherein azetidine has been prepared by reacting toluenesulfonamide and 1-bromo-3-chloropropane to obtain 1-tosylazetidine followed by reaction with lithium and wherein azetidine and 2 or 3-methyl or ethyl azetidines have been prepared by heating the appropriate 1-(2-carbethoxyethyl)azetidine together with potassium hydroxide.

More recently, but subsequent to the present invention, Nitta, Y. and Kanamori, Y., in HETEROCYCLES, Vol. 24, No. 9 (1986) pp 2467-2470 disclosed our novel 1-(diphenylmethyl)azetidine chemical intermediates and the preparation of the hydrochloride salt of azetidine therefrom. The 1-benzhydrylazetidine was prepared from tosylated-1-(benzhydryl)-3-azetidinol and sodium borohydride. That process employs entirely different starting materials and route from that of the present invention. The Nitta and Kanamori method employs leaving groups on the 2 or 3 position of the azetidine ring, which the present process does not. In addition, the process of the present invention provides a method of obtaining azetidine free base in vapor or liquid forms, which the disclosure of Nitta and Kanamori does not.

The present invention stems in part from our discovery that water in, or added to, a heated reaction mixture comprised of an α-substituted-arylmethylamine, a 1,3-dihalopropane, a non-nucleophilic base and an organic solvent induces progressive cyclization of linear intermediates as they are formed, in the same reaction mixture, to give the 1-(α-substituted-arylmethyl)azetidine which is the required precursor to the azetidine free base product of our overall process. In the absence of water, cyclization does not occur and uncyclized 3-(α-substituted-arylmethylamino)propyl halide and/or various dimers may result, for example, 1,3-bis-benzhydrylaminopropane. While the starting primary and intermediate secondary amines and the 1-(α-substituted-arylmethyl)azetidine are basic in nature, they are not capable of inducing the required cyclization to azetidine and addition of non-nucleophilic base is a requirement in the present process.

As is well known in the art, azetidine free base has great affinity for its solvents and tends to codistill with the solvent. It is also well known that azetidine free base tends to polymerize if left in contact with neutralizing agents. The present method of converting a mineral acid salt to azetidine free base overcomes these difficulties by providing a novel flash evaporating technique for an azetidine from an agitated mobile concentrated basic medium in which the azetidine salt in aqueous solution is quickly neutralized and is flash distilled out before the azetidine free base polymerizes. The solvent is undistilled for the most part due to its affinity for the remaining basic residue.

Azetidine and 2 and 3-methyl and ethyl azetidine free bases (Formula I below) have utility in the preparation of pharmaceutical agents; for example, in direct azetidination of a cycloalkanone as described in U.S. Pat. No. 4,540,690.

Prior to the present invention, no practical method suitable to scaled-up production of liquid azetidine free base, relatively free of solvent, was available.

OBJECTS AND SUMMARY OF THE INVENTION

The invention is especially concerned with novel procedures in the preparation of azetidine free base and certain derivatives encompassed by the formula:

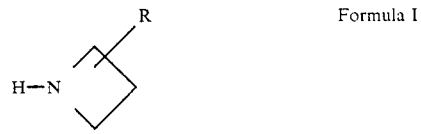

Formula I wherein R is selected from hydrogen or a loweralkyl selected from ethyl or methyl. The mineral acid addition salts of the compounds of Formula I are also present in one stage of the process.

The invention is also concerned with novel chemical intermediates, and the process for synthesis thereof, having the formula:

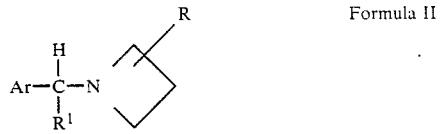

Formula II wherein;
R is hydrogen, methyl or ethyl;
$R^1$ is Ar, alkyl (3-9 C) or cycloalkyl (3-9 C);
Ar is

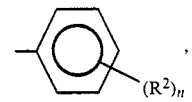

biphenyl or naphthyl;
$R^2$ is hydrogen or any non-interfering group illustrated by loweralkyl, loweralkoxy, fluoro or trifluoromethyl;
n is 1 to 3, and when n is more than one, $R^2$ may be the same or different,
and the strong mineral acid addition salts thereof.
Other novel chemical intermediates have the formula:

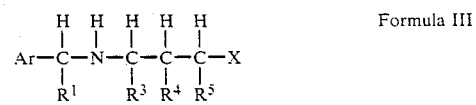

Formula III wherein;
X is any suitable leaving group exemplified by chloro, bromo, iodo, -O-tosyl or -O-mesyl;
Ar and $R^1$ are as defined above under Formula II, and
$R^3$, $R^4$, and $R^5$ are selected from hydrogen, methyl or ethyl with the proviso that no more than one alkyl group is present in the same compound.

Mixtures of compounds of Formula III wherein X may be chloro, bromo or iodo, as well as the hydrohalide acid addition salts, are also useful in the process of the invention.

In the further definition of symbols in the formulas hereof and where they appear elsewhere throughout this specification and the claims, the terms having the following significance.

The term "loweralkyl" as used herein, unless otherwise specified, includes straight and branched chain radicals of up to eight carbons inclusive and is exemplified by such groups as methyl, ethyl, propyl, isopropyl, butyl, sec-butyl, tert. butyl, amyl, isoamyl, hexyl, heptyl, and octyl radicals and the like. The term "loweralkoxy" refers to -O-loweralkyl.

The term "cycloalkyl" as used herein includes primarily cyclic alkyl radicals containing 3-9 carbon atoms exclusive and includes such groups as cyclopropyl, cyclobutyl, cyclopentyl, cyclohexyl, methylcyclohexyl, cycloheptyl and the like.

The term "halo" or "halide" when referred to herein includes chlorine, bromine and iodine.

The term "hydrohalide" refers to hydrogen chloride, hydrogen bromide and hydrogen iodide.

The term "non-interfering radical" or "non-interfering group" when used in conjunction with aryl substitution is intended to mean a radical or group which does not interfere with any of the reactions including hydrogenolysis. Such non-interfering groups and radicals are, for example, loweralkyl, loweralkoxy, trifluoromethyl or fluoro.

By "mineral acid salt" is meant a strong acid salt. Illustrative of strong acids are hydrochloric, hydrobromic, sulfuric and the like.

"Leaving groups" are radicals which facilitate nucleophilic displacement reactions and the meaning herein is intended to be that of radicals commonly used as an attachment to a hydrocarbon chain to bring about reaction with a primary amine to prepare a secondary amine or with a primary amine to prepare a tertiary amine thereby. Examples of such leaving groups are chloro, bromo, iodo, -O-tosyl or O-mesyl.

By "hydrogenolysis catalyst" is meant any catalyst which in the presence of hydrogen gas removes the 1-positioned (α-substituted)arylmethyl group from azetidine. Examples of suitable catalysts are palladium catalysts such as palladium, palladium hydroxide or palladium oxide on carbon or palladium on alumina or rhodium catalysts.

The overall process with variations included of the invention is outlined in Chart I. The preferred method of carrying out the process is to add water in admixture with reactants IV and V in hot organic solvent and non-nucleophilic base. In that instance cyclization of the linear intermediate III to the azetidine intermediate II begins immediately, which results in very little, if any, intermolecular reaction products of intermediate III and consequent higher net yields of product azetidine.

As can be seen in Chart 1, conduct of the process is not limited to use of water in the beginning mixture, in which less preferred instance, intermediate III may be prepared with or without water first, see also Chart 5. However, water must then be added if cyclization is to occur. In other also less preferred methods, intermediate III may be prepared from reactant V and other reactants, see Charts 6 and 7, for example.

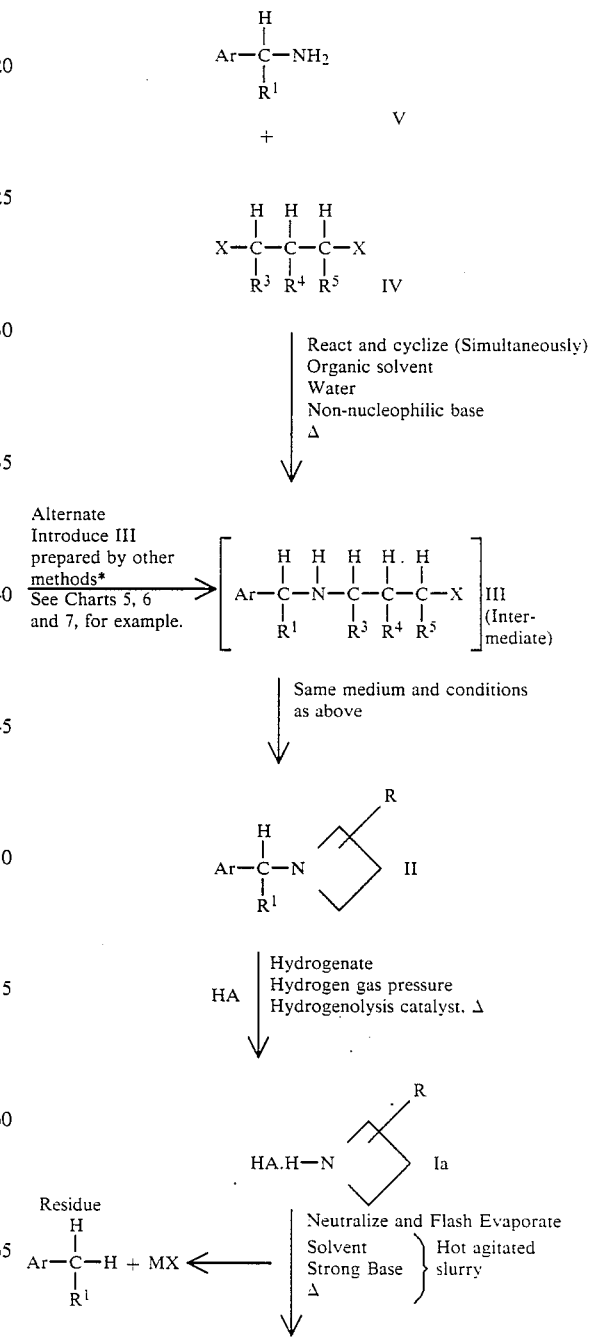

-continued
CHART 1

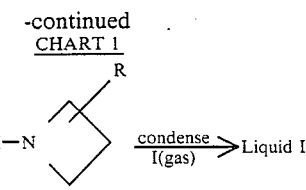

Footnotes Chart I:
X = any leaving group illustratively Cl, Br, I,

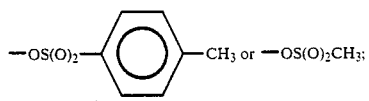

Ar, R and $R^1$ are as defined under Formulas II and III;
$R^3$, $R^4$, and $R^5$ are hydrogen, methyl or ethyl (limit 1 alkyl);
HA is mineral acid or forms mineral acid addition salt.
MX is salt formed by HA + strong base;
*Less preferred alternate process may start with III prepared by other routes.

It is therefore an object to provide an economical process for production of azetidine or 2 and 3-methyl or ethyl azetidine free bases in highly concentrated liquid form.

Another object is to provide as novel chemical intermediates certain 1-(α-substituted-arylmethyl)azetidines.

Another object is to provide as novel chemical intermediates certain 3-(α-substituted-arylmethylamino)propanes having a leaving group in the 1-position.

Still another object accomplished by the process is the provision of a novel method of obtaining azetidine free bases from strong mineral acid salts.

Additional objects will be apparent to one skilled in the art and still other objects will become apparent hereinafter.

DETAILED DESCRIPTION OF THE INVENTION

Preferentially, the preparation of the protected azetidine, the 1-(α-substituted-arylmethyl)azetidine, is accomplished in a manner such that appreciable build-up of linear 1-(α-substituted-arylmethylamino)propane derivative having a leaving group in the 3-position is avoided. However, because the linear intermediates are involved and may be employed and amine blocking techniques and various leaving group may be used, various equivalents within the scope of the process become possible.

Broadly stated, our preferred process for producing an azetidine free base of Formula I in vapor or liquid form is comprised of reacting a primary methylamine having suitable bulk providing substituents attached to the methyl carbon with an appropriate propane derivative having leaving groups in the one and three positions in hot organic solvent containing a non-nucleophilic base and an amount of water sufficient to promote azetidine ring formation to give an N-protected azetidine; hydrogenating off the protecting group of the N-protected azetidine in organic solvent or aqueous organic solvent mixture containing in either case, strong acid and obtaining from the mixture a strong acid azetidine salt concentrate and adding it to a hot, concentrated agitated solution of strong base to liberate gaseous azetidine free base thereby and condensing the vapor to obtain liquid comprised of an azetidine of Formula I.

Stated in greater particularity, allowing for some specific equivalence, the process of the invention for the preparation of liquid azetidines of Formula I may be stated to be comprised of the following steps:

Step 1, heating either a mixture selected from compounds in (a) or a single compound selected from (b) following in admixture in an organic solvent, water and a non-nucleophilic base:

(a) an α-substituted-arylmethylamine compound having the formula:

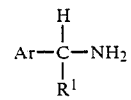

and a compound having the formula:

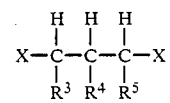

(b) a 3-α-substituted-arylmethylamino)-propane-1-X compound having the formula:

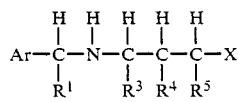

wherein in (a) and (b) Ar, $R^1$, $R^3$, $R^4$, $R^5$ and X are selected from values as defined under Formulas I, II and III hereinabove to give a reaction mixture containing an α-substituted arylmethylazetidine having the formula:

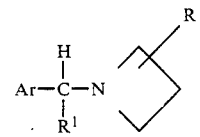

wherein Ar, $R^1$ and R are as defined under Formula II hereinabove and separating the α-substituted-arylmethyl azetidine from the reaction mixture;

Step 2, subjecting an α-substituted-arylmethylazetidine prepared in step 1, or a strong mineral acid salt thereof in a suitable organic solvent containing strong mineral acid (HA) to heat and pressurized hydrogen gas and a suitable hydrogenolysis catalyst to give a slurry comprised of a solution of azetidine salt of the compound of the formula:

wherein R is hydrogen, methyl or ethyl and HA is a strong mineral acid together with catalyst and by-product arylmethane and thereafter separating the catalyst and arylmethane by suitable means and evaporating to give a liquid concentrate comprised of the azetidine salt compound; and Step 3, adding the concentrate of the azetidine salt compound obtained in step 2 to a hot concentrated, agitated solution or slurry of strong base, thereby liberating the azetidine free base as vapor and condensing the vapor to obtain a liquid comprised of azetidine free base having the formula:

wherein R is hydrogen, methyl or ethyl.

Obviously, the process may be stopped after step 1 to give compounds of Formula II, which step is novel. Step 3, a method of liberating azetidine free base taken by itself, is also novel, being independent of the method by which the azetidine salt is obtained. In step 1, employment of intermediates (III) rather than IV and V as starting material is also a novel feature of the invention.

In reference to the methods and the process steps of the invention summarized above and labeled steps 1, 2 and 3 as they apply to the preparation of compounds of Formulas I, II and III, the following further description is applicable:

In step 1, in the preparation of compounds of Formula II, the preferred starting α-substituted-phenylmethylamine is benzhydrylamine and the preferred propane derivative having leaving groups in the 1 and 3-positions is 1-bromo-3-chloropropane. The molar ratio of the 1,3-propane derivative (IV) to the α-substituted-phenylmethylamine (V) should be at least 1:1 but may be as high as 5 to 1 or higher. Various organic solvents are suitable such as the loweralkanols, dimethylformamide, dimethylsulfoxide and the like. The preferred organic solvents are capable of dissolving the reactants and some water, protic solvents being preferred, n-butanol being an especially preferred solvent. The preferred amount of organic solvent is in the range of 0.5 to 2.0 liters per mole of starting amine. The non-nucleophilic base may be an inorganic base such as alkali-metal carbonate or an organic base such as a loweralkyl tertiary amine, potassium carbonate being a preferred non-nucleophilic base. The ratio of non-nucleophilic base to α-substituted phenylmethylamine (V) on a molar basis may vary from at least about 2.0 to 5.0 and is preferably about 2.0 to 2.5. The required amount of water to bring about azetidine ring closure is minimally about 1 mole of water per mole of non-nucleophilic base, the preferred range being about 1 to 15 moles of water per mole of base. Greater amounts of water may be added without detrimental effect; however, reaction volume becomes needlessly larger and the process becomes less economical to use. Water may be provided in the form of a hydrate of the non-nucleophilic base. Agitation is required. Temperature of the reaction mixture should be in the range of 85°-150° C., optimally about 95°-105° C. for several hours. The product of step 1, (II), exemplified by N-benzhydrylazetidine prepared in butanol-water mix, is separated from the reaction mixture as described in Example 1 and shown schematically in Chart 2.

In step 2, the α-substituted phenylmethylazetidine prepared and separated in step 1 is dissolved in a protic solvent such as a loweralkanol, preferably methanol along with an equivalent amount of a mineral acid, e.g., hydrochloric acid, hydrobromic acid, sulfuric acid, or nonaqueous hydrohalide. The solvent is mixed with a hydrogenolysis catalyst, preferably palladium on charcoal, and the mixture is subjected to hydrogen gas pressure of about 20-150 psi., preferably about 40-80 psi. and 20°-150° C., preferably 40°-80° C. for a period of time until hydrogen gas uptake ceases, usually for about 1-3 hr. The catalyst and arylmethane by-product is separated, usually by filtration or extraction and liquid aqueous concentrate of the azetidine mineral acid salt is obtained by procedures such as are shown in Example 2 and Chart 3, exemplified by starting with N-benzhydrylazetidine.

In step 3, concentrate from step 2 containing about 50-95% of the azetidine mineral acid salt, preferably about 80-95%, is added to a hot concentrated, agitated solution of strong base mix in such manner as to neutralize the mineral acid moiety of the salt and at the same time flash off the liberated azetidine free base (I), without decomposition. Best results are obtained when the concentrate is added to an agitated basic fluid mixture of the strong base in a carrier in such a way that there is no delay in volatilization of the liberated free base. Inert gases are beneficially used to sweep the free base from the neutralization zone. Hot liquid solutions of strong bases are preferred for use in the neutralizing-vaporizing zone, preferably about 40-80 weight percent aqueous solutions of potassium or sodium hydroxide at 60°-200° C., preferably at about 80°-110° C. under vigorous agitation. In general, the amount of base in the neutralizing-vaporizing zone should be high enough to hold water in solution. Otherwise, excess water will contaminate the overhead azetidine free base. Usual methods of condensation such as water and ice cooled columns or receivers may be used to condense the azetidine free base.

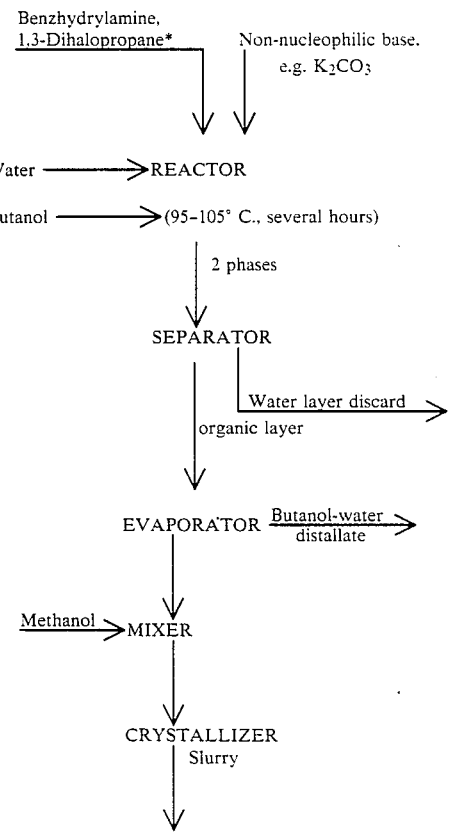

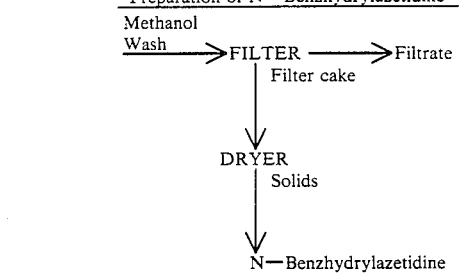
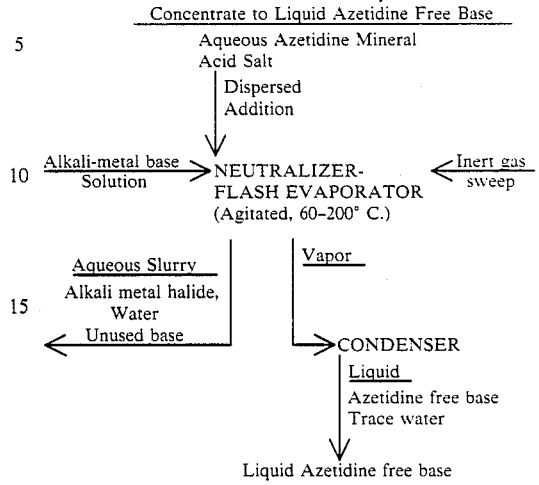
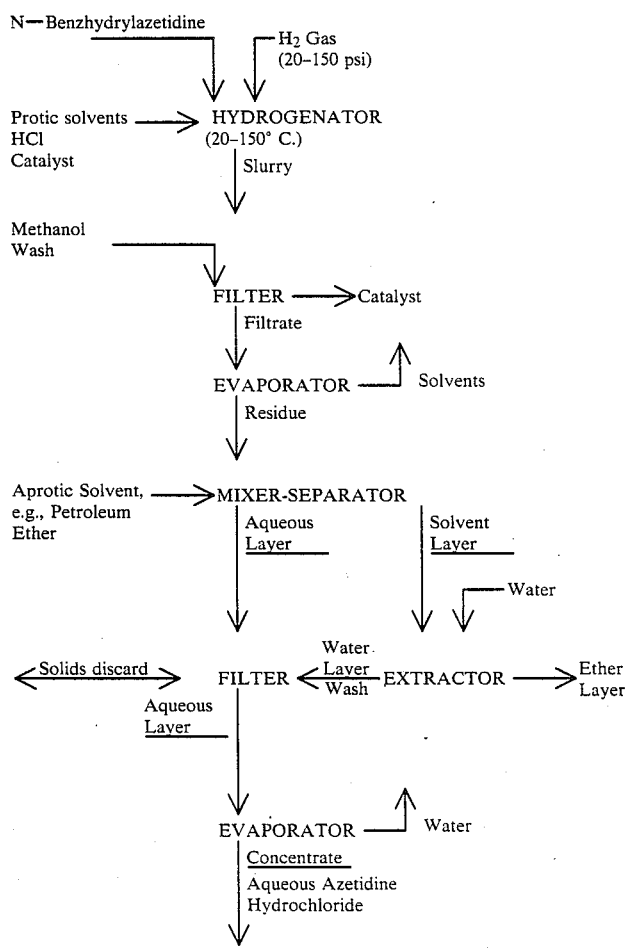

CHART 5

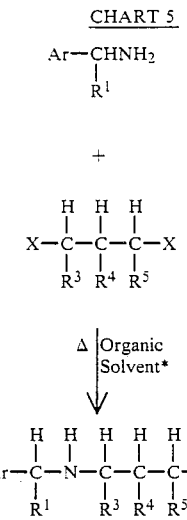

Footnote Chart 5:
X is halo;
Ar and $R^1$ are as defined under Formula II; and $R^3$, $R^4$ and $R^5$ are as defined under Formula III.
*Non-nucleophilic base and water not required. Both base and water may be added when temperature is kept below about 80° C.

CHART 6

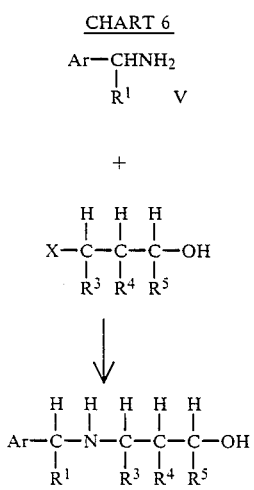

Footnote Chart 6:
Ar and $R^1$ are as defined under Formula I. $R^3$, $R^4$ and $R^5$ are as defined under Formula III.

CHART 7

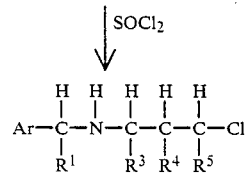

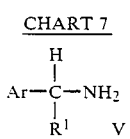

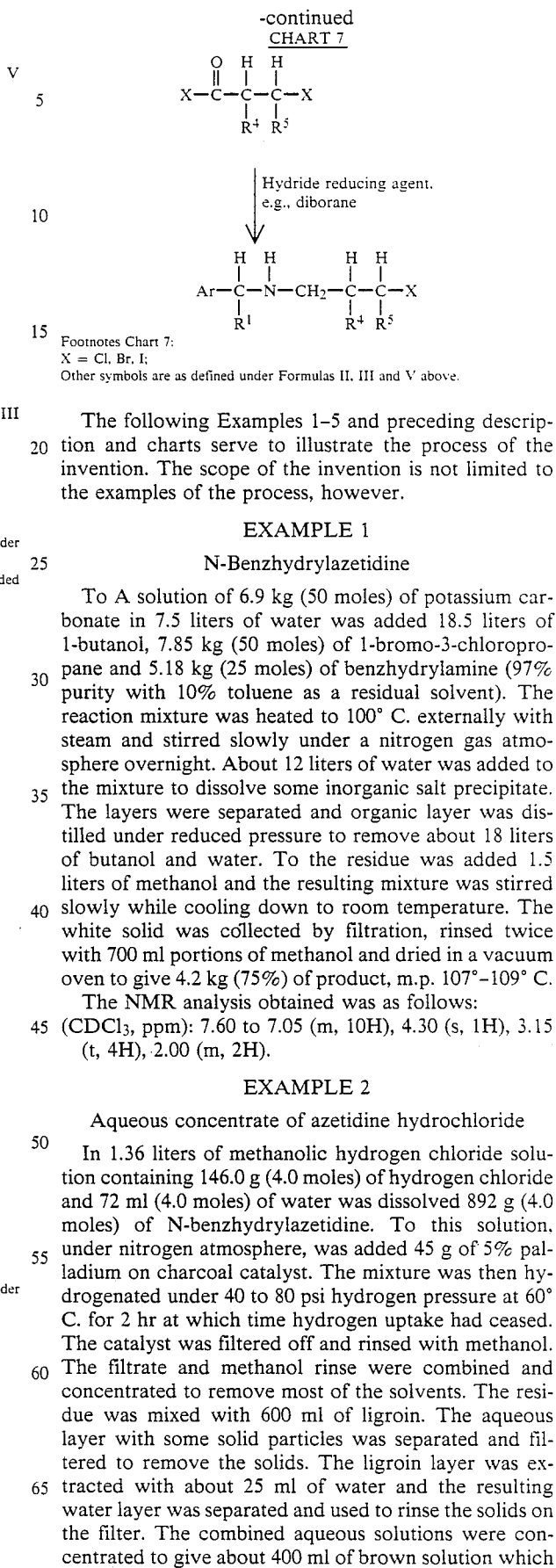

Footnotes Chart 7:
X = Cl, Br, I;
Other symbols are as defined under Formulas II, III and V above.

The following Examples 1–5 and preceding description and charts serve to illustrate the process of the invention. The scope of the invention is not limited to the examples of the process, however.

EXAMPLE 1

N-Benzhydrylazetidine

To A solution of 6.9 kg (50 moles) of potassium carbonate in 7.5 liters of water was added 18.5 liters of 1-butanol, 7.85 kg (50 moles) of 1-bromo-3-chloropropane and 5.18 kg (25 moles) of benzhydrylamine (97% purity with 10% toluene as a residual solvent). The reaction mixture was heated to 100° C. externally with steam and stirred slowly under a nitrogen gas atmosphere overnight. About 12 liters of water was added to the mixture to dissolve some inorganic salt precipitate. The layers were separated and organic layer was distilled under reduced pressure to remove about 18 liters of butanol and water. To the residue was added 1.5 liters of methanol and the resulting mixture was stirred slowly while cooling down to room temperature. The white solid was collected by filtration, rinsed twice with 700 ml portions of methanol and dried in a vacuum oven to give 4.2 kg (75%) of product, m.p. 107°–109° C.

The NMR analysis obtained was as follows:
($CDCl_3$, ppm): 7.60 to 7.05 (m, 10H), 4.30 (s, 1H), 3.15 (t, 4H), 2.00 (m, 2H).

EXAMPLE 2

Aqueous concentrate of azetidine hydrochloride

In 1.36 liters of methanolic hydrogen chloride solution containing 146.0 g (4.0 moles) of hydrogen chloride and 72 ml (4.0 moles) of water was dissolved 892 g (4.0 moles) of N-benzhydrylazetidine. To this solution, under nitrogen atmosphere, was added 45 g of 5% palladium on charcoal catalyst. The mixture was then hydrogenated under 40 to 80 psi hydrogen pressure at 60° C. for 2 hr at which time hydrogen uptake had ceased. The catalyst was filtered off and rinsed with methanol. The filtrate and methanol rinse were combined and concentrated to remove most of the solvents. The residue was mixed with 600 ml of ligroin. The aqueous layer with some solid particles was separated and filtered to remove the solids. The ligroin layer was extracted with about 25 ml of water and the resulting water layer was separated and used to rinse the solids on the filter. The combined aqueous solutions were concentrated to give about 400 ml of brown solution which was shown by proton NMR to be azetidine hydrochloride with about 1.5 mole of water.

The NMR analysis found is as follows:
(D$_2$O, ppm): 4.95 (s, exchangeable proton, ~5H), 4.20 (t, 4H), 2.60 (m, 2H).

EXAMPLE 3

Azetidine liquid free base

A solution of azetidine hydrochloride having about 1.5 moles of water per mole of azetidine hydrochloride was first prepared as in Example 2, using ¼ of the amounts (e.g., 1 mole of N-benzhydrylazetidine and other materials scaled down). This solution was added dropwise to a stirred solution of 115 g (2.5 mole) of potassium hydroxide in 70 ml of water maintained at 100° C. The vapor was swept by a slow stream of nitrogen through a short Vigreux column to a water cooled condenser. The receiver was chilled in an ice bath. Colorless liquid distillate in amount of 47.5 g (83% yield based on starting N-benzhydrylazetidine) was obtained. The liquid was analyzed by Karl Fischer assay and found to contain 2.4% water.

The following $^1$HNMR analysis was found:
D$_2$O, ppm): 5.00 (s, 1.1H), 3.55 (t, 4H), 2.30 (m, 2H).

EXAMPLE 4

1-Benzhydrylamino-3-chloropropane

A mixture of 0.1 mole of benzhydrylamine, 39.3 g (0.25 moles) of 1-bromo-3-chloropropane, 13.8 g (0.1 mole) of potassium carbonate, 20.0 ml of dimethylformamide and 20.0 ml of water were heated at 75° C. for 2 hr. The organic layer was separated and concentrated on a rotary high vacuum evaporator to give 26 g of title compound of 85–90% purity of title compound containing about 5% each of benzhydrylamine and 1-benzhydrylazetidine.

The following $^1$NNMR analysis was obtained:
(CDCl$_3$, ppm): 7.30 (m, aromatic protons), 5.15 (s, methine proton of $\phi_2$CHNH$_2$), 4.75 (s, methine proton of $\phi_2$CHNHCH$_2$CH$_2$CH$_2$-halo), 4.30 (s, methine proton of benzhydrylazetidine), 3.60 (t, methylene protons next to halogen on $\phi_2$CHNH—CH$_2$CH$_2$CH$_2$-halo), 3.10 (t, methylene protons next to the nitrogen on the azetdine ring), 2.65 (t, methylene protons next to the nitrogen on $\phi_2$CHNHCH$_2$CH$_2$CH$_2$-halo), 1.90 (pentet, methylene protons on the central carbon of $\phi_2$CHNHCH$_2$CH$_2$CH$_2$-halo), and 1.50 (s, NH protons).

From the integration of the singlets at 5.15, 4.75 and 4.30, the ratio of the following in the material is estimated:

| $\phi_2$CHNH$_2$: | $\phi_2$CHNHCH$_2$CH$_2$CH$_2$—halo: | $\phi$CHN |
|---|---|---|
| 1: | 18: | 2 or |
| 4.8% | 85.6% | 9.6% |

Close examination of the NMR chart showed a trace of 1-benzhydrylamino-3-bromopropane was present.

EXAMPLE 5

Mixture of hydrochloride and hydrobromide salts of 1-Benzhydrylamino-3-chloropropane, and 1-Benzhydrylamino-3-bromopropane A mixture of 0.25 mole of benzhydrylamine, 74 ml (0.75 mole) of 1-bromo-3-chloropropane in 120 ml of ethyl acetate was heated at reflux under a nitrogen atmosphere for 3 days. The reaction mixture was cooled, filtered and the solid was washed with ethyl acetate followed by petroleum ether. A sample was dried and subjected to $^1$HNMR analysis which showed the product to have both bromine and chlorine on the chain terminal. This was confirmed by mass spectrum analysis. The product also contained some starting benzhydrylamine hydrohalide. Total yield of white powder was 63.0 g.

What is claimed is:

1. A process for the preparation of an azetidine free base in vapor or liquid form having the formula:

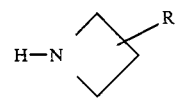

wherein R is selected from hydrogen, methyl or ethyl which consists essentially of reacting an α-substituted arylmethylamine with an appropriate propane derivative having leaving groups in the 1 and 3 positions in hot organic solvent, a non-nucleophilic base, and an amount of water sufficient to promote azetidine ring formation to give an N-protected azetidine; hydrogenating off the protecting group of the N-protected azetidine in an organic solvent or an aqueous organic solvent mixture containing, in either case, strong mineral acid and obtaining a strong acid azetidine salt concentrate therefrom and adding the concentrate to a hot concentrated agitated solution or slurry of strong base to liberate gaseous said azetidine free base and optionally condensing the vapor to obtain said azetidine free base as a liquid.

2. A process for the preparation of an azetidine free base having the formula:

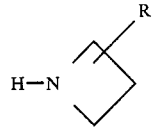

wherein R is selected from hydrogen, methyl or ethyl which consists essentially of the following steps:

Step 1, heating either a mixture selected from compounds in (a), or a single compound selected from (b), following in admixture in an organic solvent, water and a non-nucleophilic base:

(a) two compounds, one an α-substituted-arylmethylamine selected from those having the formula:

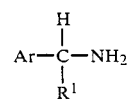

and the other selected from a propane derivative having the formula:

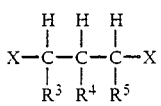

or, (b) a compound selected from 3-(α-substituted arylmethylamino)-propane-1-X compound having the formula:

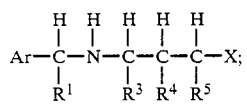

wherein in (a) and (b) above, Ar is

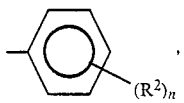

biphenyl or naphthyl;
$R^1$ is Ar, alkyl (3-9 C) or cycloalkyl (3-9 C);
X is any suitable leaving group;
$R^2$ is hydrogen or a non-interfering group;
n is 1 to 3, and when n is more than one, $R^2$ may be the same or different; and
$R^3$, $R^4$, and $R^5$ are hydrogen or a loweralkyl selected from methyl or ethyl with the proviso that only one of the $R^3$, $R^4$ or $R^5$ groups is a methyl or ethyl group at the same time, to give a reaction mixture containing an α-substituted arylmethylazetidine having the formula:

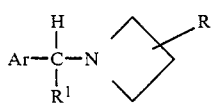

wherein Ar and $R^1$ have the starting values and R is hydrogen, methyl or ethyl and separating said α-substituted-arylmethylazetidine from the mixture;

Step 2, subjecting an α-substituted-arylmethylazetidine prepared in step 1, or a strong mineral salt thereof in a suitable organic solvent containing strong mineral acid to heat and pressurized hydrogen gas (HA) with a suitable hydrogenolysis catalyst to give a slurry comprised of a solution of an azetidine salt compound of the formula:

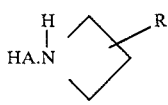

wherein R is hydrogen, methyl or ethyl and HA represents a strong mineral acid; the catalyst and by-product arylmethane wherein $R^1$ has the starting value and thereafter separating the catalyst and said by-product and evaporating said solvent to give a liquid concentrate comprised of said azetidine salt compound; and Step 3, adding the concentrate obtained in step 2 to a hot, concentrated, agitated solution or slurry of strong base, liberating the said azetidine free base vapor and condensing the vapor to obtain a liquid comprised of said azetidine free base.

3. The process of claim 2 wherein in step 1 the organic solvent used in butanol.

4. The process of claim 2 wherein in step 1 the non-nucleophilic base used is potassium carbonate.

5. The process of claim 2 wherein in step 1 the α-substituted arylmethylamine used is benzhydrylamine.

6. The process of claim 2 wherein in step 1 the 3-(α-substituted-arylmethylamino)propane derivative used is 3-benzhydrylaminopropyl halide.

7. The process of claim 2 wherein in step 1 the amount of water used is at least 1 mole per mole of non-nucleophilic base.

8. The process of claim 2 wherein in step 1 the temperature is held at about 95°-105° C.

9. The process of claim 2 wherein in step 1 the propane derivative used is 1-bromo-3-chloropropane.

10. A process for the preparation of an α-substituted-arylmethylazetidine having the formula:

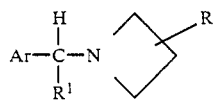

wherein R is hydrogen, methyl or ethyl, Ar is

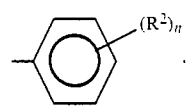

biphenyl, or naphthyl; and $R^1$ is Ar, alkyl (3-9 C), or cycloalkyl (3-9 C), which consists essentially of heating one of the following (a) or (b) alternatively in admixture in an organic solvent, water and a non-nucleophilic base:

(a) two compounds, one an α-substituted arylmethylamine selected from those having the formula:

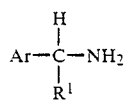

and the other selected from a propane derivative having the formula:

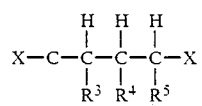

(b) a compound selected from an 3-(α-substituted arylmethylamino)propyl halides having the formula:

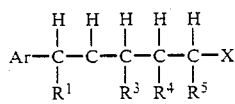

wherein in (a) or (b)
Ar is

biphenyl or naphthyl;
R¹ is Ar, alkyl (3–9 C) or cycloalkyl (3–9 C);
X is any suitable leaving group;
R² is hydrogen or a non-interfering group;
n is 1 to 3 and when n is more than 1, R² may be the same or different; and
R³, R⁴ and R⁵ are hydrogen or a loweralkyl selected from methyl or ethyl with the proviso that only one of the R³, R⁴ or R⁵ groups is a methyl or ethyl group at the same time,
and isolating said α-substituted arylmethylazetidine from the solution.

11. The process of claim 10 wherein the organic solvent used in butanol.

12. The process of claim 10 wherein the non-nucleophilic base used is potassium carbonate.

13. The process of claim 10 wherein the α-substituted arylmethylamine used is benzhydrylamine.

14. The process of claim 10 wherein the 3-(α-substituted arylmethylamino)propane derivative used is 3-benzhydrylaminopropyl halide.

15. The process of claim 10 wherein the amount of water used is at least 1 mole per mole of non-nucleophilic base.

16. The process of claim 10 wherein the temperature is held at about 95°–105° C.

17. The process of claim 10 wherein the propane derivative used is 1-bromo-3-chloropropane.

18. A process for the preparation of azetidine free base which consists essentially of the steps of
Step 1, heating one of the following (a) or alternatively (b) in admixture with an organic solvent, water and a non-nucleophilic base:
 (a) benzhydrylamine and a dihalopropane, or
 (b) 1-(benzhydrylamino)-3-halopropane to give a reaction mixture containing N-benzhydrylazetidine and separating said N-benzhydrylazetidine therefrom;
Step 2, subjecting the N-benzhydrylazetidine prepared in step 1 in a suitable organic solvent containing strong mineral acid (HA) to heat and pressurized hydrogen gas and a suitable hydrogenolysis catalyst to give a slurry comprised of a solution of an azetidine salt compound having the formula:

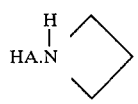

wherein HA represents a strong mineral acid and the catalyst and by-product diphenylmethane and thereafter separating the catalyst and diphenylmethane by suitable means and evaporating to give a liquid concentrate comprised of said azetidine salt compound; and
Step 3, adding the concentrate of the azetidine salt obtained in step 2 to a hot concentrated, agitated solution or slurry of strong base, thereby liberating azetidine free base as vapor and condensing the vapor to give a liquid comprised of azetidine free base.

19. A process for the preparation of azetidine free base which consists essentially of the steps of
Step 1, heating benzhydrylamine and a 1-bromo-3-chloropropane in admixture with butanol, water and potassium carbonate to give N-benzhydrylazetidine and separating it from the mixture;
Step 2, subjecting the N-benzhydrylazetidine in aqueous methanolic hydrogen chloride to hydrogen gas pressure over hydrogenolysis catalyst while heating to give a slurry comprised of azetidine hydrochloride, catalyst and by-product diphenylmethane and thereafter separating the catalyst and diphenylmethane by suitable means and evaporating to give a liquid concentrate of azetidine hydrochloride;
Step 3, adding the concentrate obtained in step 2 to a hot, concentrated, agitated basic solution or slurry liberating gaseous azetidine and condensing the vapor to give liquid comprised of azetidine.

20. A process for the preparation of an azetidine free base having the formula:

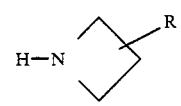

wherein R is selected from hydrogen, methyl, or ethyl which consists essentially of the steps of
Step 1, heating a 3-(α-substituted-arylmethylamino)propane derivative having a leaving group in the 1-position in admixture in an organic solvent with water and a non-nucleophilic base, said propane derivative selected from those having the formula:

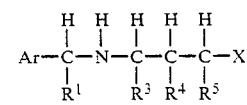

wherein
Ar is

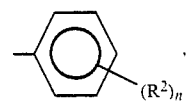

biphenyl or naphthyl;
R¹ is Ar, alkyl (3–9 C) or cycloalkyl (3–9 C);
X is a leaving group selected from bromine, chlorine, iodine, O-tosyl or O-mesyl;
R² is hydrogen or a non-interfering group;
n is 1 to 3 and when n is more than one, R² may be the same or different; and
R³, R⁴ and R⁵ are hydrogen or a loweralkyl selected from methyl or ethyl with the proviso that only one of the R³, R⁴ or R⁵ groups is a methyl or ethyl at the same time;

to give a reaction mixture containing an α-substituted-arylmethylazetidine having the formula:

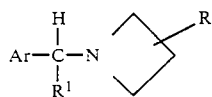

wherein

Ar and $R^1$ have the starting values and R is hydrogen, methyl or ethyl and separating said α-substituted-arylmethylazetidine from the mixture;

Step 2, subjecting an α-substituted-arylmethylazetidine prepared in step 1 in a suitable organic solvent containing strong mineral acid (HA) to heat, pressurized hydrogen gas and a hydrogenolysis catalyst to give a slurry comprised of a solution of an azetidine salt represented by the formula:

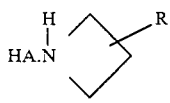

wherein R is hydrogen, methyl or ethyl and HA represents a strong mineral acid; the catalyst and by-product aryl-$R^1$ methane wherein $R^1$ has the starting value and thereafter separating the catalyst and said by-product and evaporating said solvent to give a liquid concentrate comprised of said azetidine salt; and Step 3, adding the concentrate obtained in step 2 to a hot concentrated, agitated basic slurry to liberate said azetidine free base as a vapor and condensing the vapor to obtain said azetidine free base in liquid form.

21. A process for the preparation of azetidine free base which consists essentially of the steps of Step 1, heating benzhydrylamine and 1-bromo-3-chloropropane in admixture with butanol, water and potassium carbonate to give N-benzhydrylazetidine and separating said N-benzhydrylazetidine therefrom;

Step 2, subjecting the N-benzhydrylazetidine obtained in step 1 in methanol together with hydrochloric acid to heat and pressurized hydrogen gas and palladium on carbon catalyst to give a slurry containing therein catalyst, azetidine hydrochloride and by-product diphenylmethane and thereafter separating the catalyst and diphenylmethane and evaporating to give a liquid concentrate of azetidine hydrochloride; and Step 3, adding the azetidine hydrochloride concentrate obtained in step 2 to a hot consentrated, agitated solution or slurry of strong base, thereby liberating azetidine free base as vapor and condensing the vapor to give a liquid comprised of azetidine free base.

* * * * *